United States Patent [19]

Spetzler et al.

[11] Patent Number: 4,596,564

[45] Date of Patent: Jun. 24, 1986

[54] MEDICAL APPLIANCE

[75] Inventors: Robert F. Spetzler; Alfred A. Iversen, both of Hopkins, Minn.

[73] Assignee: PMT, Inc., Hopkins, Minn.

[21] Appl. No.: 596,510

[22] Filed: Apr. 3, 1984

Related U.S. Application Data

[63] Continuation-in-part of Ser. No. 421,237, Sep. 22, 1982, abandoned, which is a continuation of Ser. No. 229,737, Jan. 29, 1981, abandoned.

[51] Int. Cl.$^4$ ............................................. A61M 25/00
[52] U.S. Cl. ........................................ 604/281; 604/8; 604/45
[58] Field of Search .................... 604/8–10, 604/27, 35, 39, 43, 45, 48, 93, 118, 119, 264, 280–283

[56] References Cited

U.S. PATENT DOCUMENTS

| | | | |
|---|---|---|---|
| 1,060,665 | 5/1913 | Bell | 604/281 |
| 1,596,754 | 8/1926 | Moschelle | 604/282 |
| 3,319,628 | 5/1967 | Halligan | 604/119 |
| 3,430,631 | 3/1969 | Abramson | 604/282 |
| 3,752,510 | 8/1973 | Windischmann et al. | 604/283 |
| 4,000,739 | 1/1977 | Stevens | 604/280 |
| 4,014,333 | 3/1977 | McIntyre | 604/43 |
| 4,178,936 | 12/1979 | Newcomb | 604/43 |
| 4,291,691 | 9/1981 | Cabal et al. | 604/35 X |
| 4,323,065 | 4/1982 | Kling | 604/283 |

Primary Examiner—C. Fred Rosenbaum
Assistant Examiner—Michelle Lester
Attorney, Agent, or Firm—Hugh D. Jaeger

[57] ABSTRACT

A medical appliance of a stationary surgical suction device comprised of an ultramalleable formable tube that may readily be shaped in situ. The tube is comprised of a formable, flexible tubular plastic ultramalleable material, having at least one fluid conveying lumen and includes a parallel oriented malleable member that is disposed within the plastic material so as to be frictionally interrelated to the tubular plastic material. A method of fabricating the lumen includes the steps of furnishing a plastic tubing having at least a pair of lumens, furnishing an elongated malleable member of cross-section complementary to that of one of the lumens and of a size in excess of the size of the lumen, dilating the lumen to allow insertion of the malleable member into the lumen and allowing the lumen to shrink onto the malleable member to effect a frictional engagement with the lumen. The appliance fabricated by the method may be used in surgical retracting, suction or irrigation procedures, as a shunt for fluid vessels or for the drainage of a cavity.

1 Claim, 13 Drawing Figures

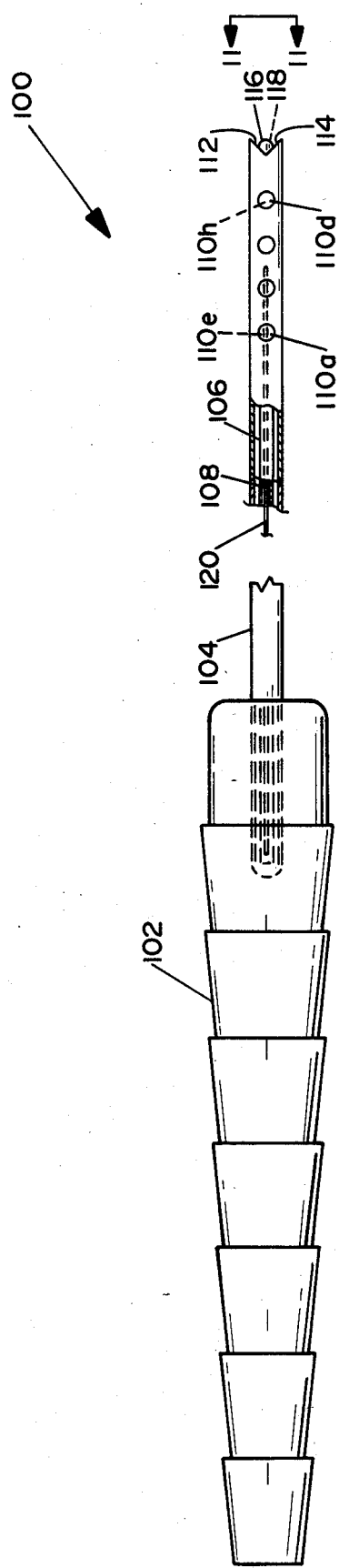
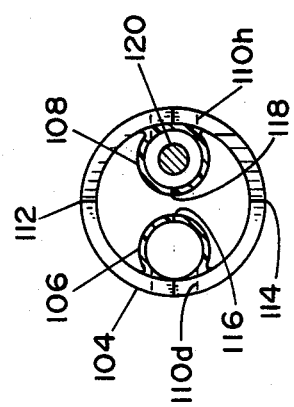
FIG. 10
FIG. 11

MEDICAL APPLIANCE

This application is a continuation-in-part of Ser. No. 421,237, filed Sept. 22, 1982, now abandoned, which was a continuation of Ser. No. 229,737, filed Jan. 29, 1981, now abandoned.

BACKGROUND OF THE INVENTION

1. Field of the Invention

This invention relates to disposable medical appliances, and is more particularly directed to formable lumens for irrigating, transporting or removing fluids from one location to another with respect to the body of a patient and to a method of fabricating such lumens.

2. Description of the Prior Art

Examples of prior art to the field with which our invention is concerned may be seen in U.S. Pat. Nos. 3,128,769; 3,169,528; 3,903,885; 3,935,857; and, 4,033,331.

Of these, U.S. Pat. No. 3,169,528 is illustrative of a surgical drainage collection device, known as a "coronary sinus sucker," in which a length of wire or ductile material or metal is shown interposed or embedded in the outer wall of a plastic tube and is further described as a "wire reinforcement" that causes the sucker to retain any configuration to which it is bent.

None of the prior art appears to disclose the advantages of our method, the product resulting from such method or a product having the features to be set forth below.

The present invention has been successfully applied to the field of micro-surgery wherein its demonstrable usefulness in ease of use and efficiency with respect to reducing the amount of time involved for surgical procedures while increasing cost efficiency by reducing the expense of achieving the desired results is believed to present a dynamic testimony to the efficiency of applicant's invention.

SUMMARY OF THE INVENTION

Our medical appliance is comprised of a formable tube having at least two lumens parallel disposed through the length of the tube. One of the lumens is configured to receive and frictionally engage a complementary shaped length of malleable material which, when deformed, will retain the deformed shape so that the tube may be formable to any configuration desired by the user. The malleable member extends the length of the tube and is disposed in a lumen within the confines of the tube. The other lumen or lumens that may be provided within the tube may then be used for conveying of material to and from one end of the tube when assembled in a suitable connector-mounting.

One method of fabricating the formable tube comprises the steps of providing a tube of plastic material such as silicone rubber or polyurethane, of suitable durometer according to a graph and having at least a pair of parallel disposed lumens extending completely there through; providing a length of malleable material, of malleability related to the durometer of the plastic material and of a size in excess of one of the lumens; chemically, or otherwise, dilating the lumen so that is may receive the over-sized length of malleable material; inserting the malleable material into and through the dilated lumen; and thereafter allowing the lumen to assume its normal size to thereby frictionally engage the length of malleable material throughout its length.

It may therefore be seen that our invention provides a medical appliance that may have one or more lumens available for the introduction or withdrawal of fluids or gases to or from the body of a patient during a medical or surgical procedure. The appliance may be readily formed to a shape dictated by the dynamic phenomena associated with any such medical or surgical procedure. For example, when used as a cardiac shunt, incisions are made at the desired location in a carotid artery, a tube is cut to length and the ends are inserted into the artery while, at the same time, the tube is formed to a shape dictated by the geometries of the location in a particular patient, the ends of the tube are held in place by suitable sutures around the artery and the appliance may be left in place for the desired period of time without further attention. When used as a suction and irrigating appliance, the lumens in a tube may be connected to suitable sources of irrigation material and to a source of vacuum and, again, the tube may be formed to any desired shape for further use by hand, may be taped in place after suitable formation or may be inserted in place for internal procedures.

Significant aspects and features of the present invention include a ultramalleable stationary surgical suction for micro-surgery, neuro-surgery, and surgery which provides a malleability with a relationship existing between the durometer and diameter. This relationship is illustrated in the graph drawing.

Another significant aspect and feature of the present invention is a stationary surgical suction medical device which does not collapse under a vacuum due to the inherent design between the specific shape of the tubing. The specific shape of the tubing is chosen to reduce collapsing of the tubing under an applied vacuum.

A further significant aspect and feature of the present invention is a stationary surgical suction device which is particularly useful for smoke removal during laser surgery or cauterizing. The device is also useful for chest drainage during thoratic surgery.

An additional significant aspect and feature of the present invention is a stationary surgical suction device for micro-surgery, neuro-surgery, and surgery which is available in sizes from 3 french to 22 french. The 5 french size is the most popular in utilization.

Having thus described principal embodiments of the present invention, it is a principal object hereof to provide a ultramalleable stationary surgery suction for micro-surgery, neuro-surgery, or surgery.

One object of the present invention is to provide a surgical suction device which is stationary and accepts a predetermined geometrical configuration for utilization within a patient during surgery.

Another object of the present invention is inherent anti-collapsing characteristics of the device when under a vacuum condition.

Another object of the present invention is a stationary surgical suction device where the most popular and preferred size is the 3–5 french size. The larger size such as a 22 French is particularly beneficial in laser smoke removal.

BRIEF DESCRIPTION OF THE DRAWINGS

The features, objects, and advantages of this invention will be more clearly perceived from the following detailed description when taken in conjunction with the accompanying drawings in which:

FIG. 1A is a pictorial representation of another application of our medical appliance in a surgical procedure;

FIG. 10 is a view of a five french size;

FIG. 11 is a view taken along line 11—11 of FIG. 12, and;

DESCRIPTION OF THE PREFERRED EMBODIMENTS

Figure 1:
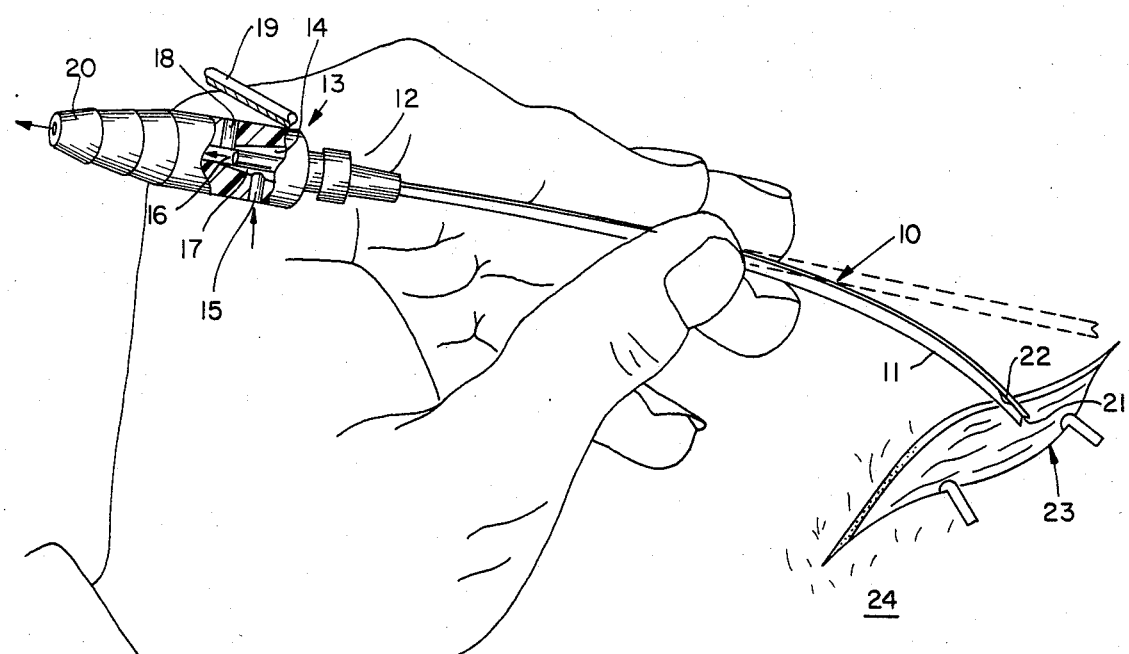
FIG. 1 is a pictorial, partly broken away view illustrating our invention in use in a surgical procedure.
Figure 2:
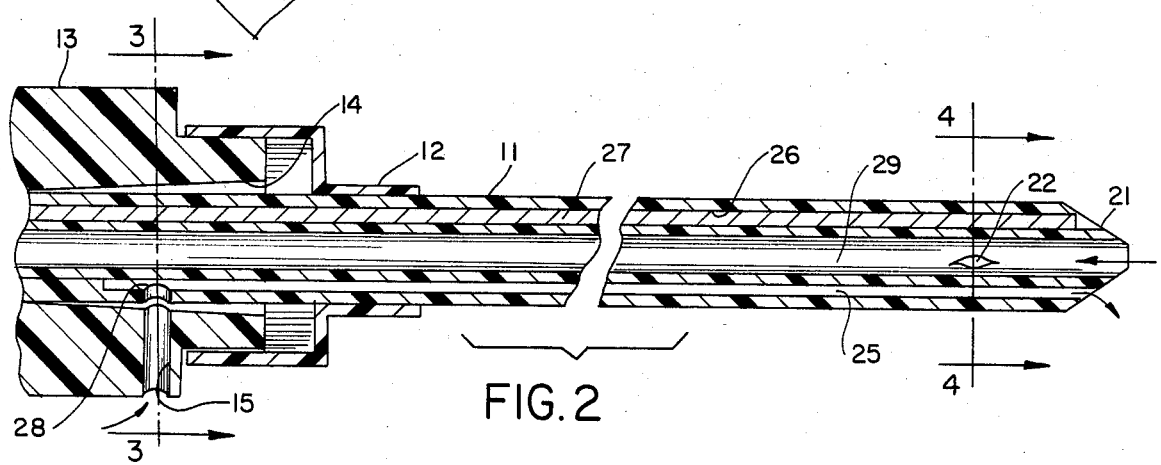
FIG. 2 is an enlarged sectional fragmentary view of the medical appliance of FIG. 1.
Figure 3:
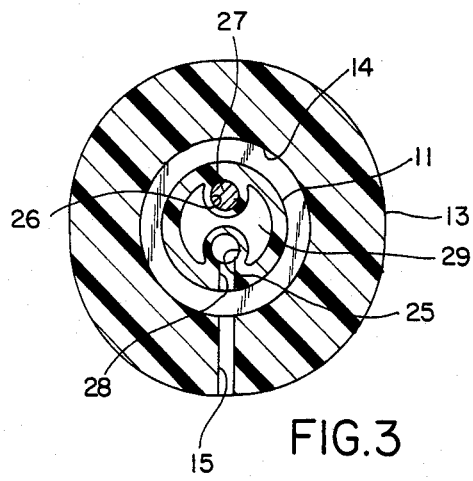
FIG. 3 is a sectional view taken along Section Line 3—3 on FIG. 2.
Figure 4:
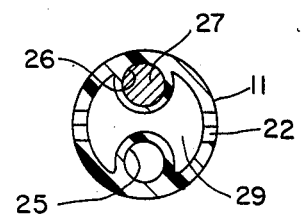
FIG. 4 is a sectional view taken along Section Line 4—4 on FIG. 2.

FIG. 1-4 of the drawings, there is shown a formable medical appliance indicated generally by a reference character 10. Appliance 10 is comprised of a tube 11 that is shown connected to a mounting 13 through a connector 12. Mounting 13 has a chamber 14 at its right end that is accessible through a hole indicated by reference character 15. Mounting 13 also has a bore 16 that is disposed within a tapered character 20 and is further in communication with a hole 18 extending outwardly from the right hand end of bore 16. A movable flap member 19 is shown disposed in an intermediate position overlying hole 18. Tube 11 is connected to the left hand end of chamber 14 as indicated by reference character 17. Plastic tube 11 is further provided with a tapered tip 21 at its right hand end and is shown having a plurality of apertures 22 extending into the interior thereof in communication with a lumen, indicated by reference character 29, in fluid communication with bore 16 in mounting 13. Lumen 25 in tube 11 is shown in fluid communication with chamber 14 through aperture 28 at its left hand end and is in fluid communication with the tip 21 at its right hand end. Lumen 26 in tube 11 is shown having a similarly configured malleable insert 27 extending through its entire length from the right hand end to the left hand end of tube 11.

Tube 11 may be formed of suitable plastic material such as silicone rubber or polyurethane of suitable hardness in a durometer range, that increases with size, of approximately 55 to 90 and malleable insert 27 may be comprised of, for example, 60/40 lead-tin alloy or other suitable material of a malleability compatible with the durometer of the plastic material so that when tube 11 is deformed into a different shape, it will retain the deformed shape and not return to the original shape.

Tube 11 may be fabricated by providing an elongated plastic member with at least a pair of lumens including a lumen 26 and dilating the length of lumen 26 with an appropriate procedure such as immersing a silicone rubber tube in the vapor or fluid of freon, xylene, benzene, chlorform, or either or, in the case of polyurethane, the vapor or fluid of acetone. Other forms of dilation may include heating and the like. A length of malleable material 27, such as lead-tin alloy, is fabricated to a size slightly greater that the normal diameter of lumen 26 and thereupon inserted there through and the tubing is allowed to revert to its original undilated shape or form to thereby frictionally grip malleable insert 27 along its entire length.

As shown in FIGS. 1 and 1A, our surgical appliance may be used during an operative procedure on an incision 23 or 31 in the body 24 or 32 of a patient. In the illustration of FIG. 1, the tip of tube 11 is shown bent so as to be held and guided by the hand of a surgeon or assistant in the course of an operation and in the illustrative embodiment, irrigation fluid may be supplied through hole 15 and lumen 25 to the incision while a vacuum may be applied to the incision through tip 21 or apertures 22, lumen 29 and bore 16 of mounting 13. In the illustration of FIG. 1A, tube 11 has been formed to provide a retractor action and may, as illustrated, be taped in place to maintain the retraction force while at the same time provide the function of irrigating or withdrawing fluid by suction as in the case of the illustration of FIG. 1. The operation of flap 19 on mounting 13 may be such that a partial or full vacuum may be supplied for withdrawing fluids at the desire of the surgeon.

It is anticipated that our appliance may be fabricated in a size suitable for mounting upon a microscope in connection with micro-surgical techniques. It is also contemplated that our medical appliance may be useful in the drainage of cavities after operative procedures or as required in the course of medical treatment.

Figure 5:
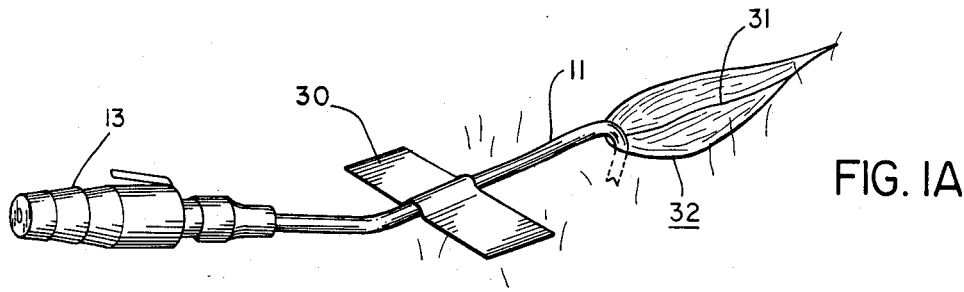
FIGS. 5, 6, and 7 are enlarged cross-sectional views of further embodiments of our invention.
Figure 5:
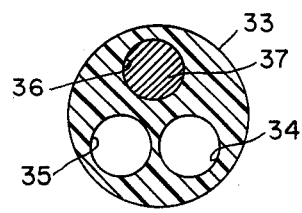
Figure 6:
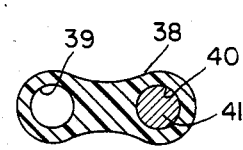
Figure 7:
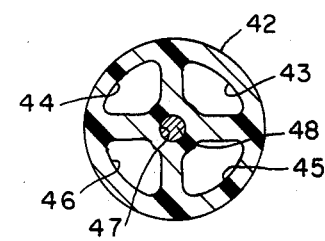
Figure 8:
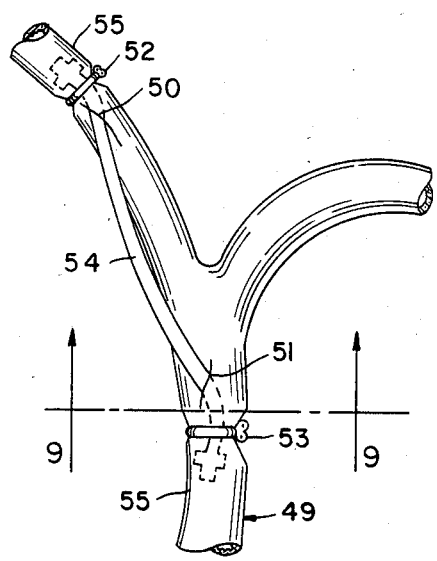
FIG. 8 is a pictorial view of our medical appliance in position as a shunt in a carotid artery.

As may be seen in FIGS. 5, 6, and 7, tube 11 may be fabricated, as by extrusion, in other configurations. Referring specifically to FIG. 5, a tube 33 is shown having lumens 34, 35, and 36 with a malleable insert 37 disposed within lumen 36. In FIG. 6, tube 38 is when having lumens 39 and 40 with a malleable insert 41 disposed in lumen 40. FIG. 7 illustrates a further multilumened tube 42 having lumens 43, 44, 45, 46, and 47 and a malleable insert 48 disposed in lumen 47.

In all of the illustrated embodiments, the lumen containing the malleable insert is dispose substantially within the confines of the outline of the tubes, e.g. 11, 33, 38, and 42. This is believed to provide a stability, in actual use, that has heretofore been lacking in known prior art appliances.

Figure 9:
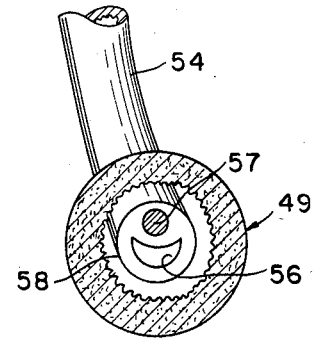
FIG. 9 is an enlarged sectional view of a portion of FIG. 8 taken along Section Line 9—9.

Referring to FIGS. 9 and 10, our invention is illustrated embodied as a shunt for a carotid artery 49. A tube 54 having a central lumen 56 for passage of blood and a further lumen 57, having a malleable member 58 disposed therein, is shown provided with rounded enlarged portions 55 at either end and held in place in carotid artery 49 by suitable sutures 42 and 43. Tube 54 may be formed to any shape required by the location of the incisions or the anatomy of the patient and may thereafter be left in place for the period of time necessary for the surgical or medical procedure.

MODE OF OPERATION

Figure 12:
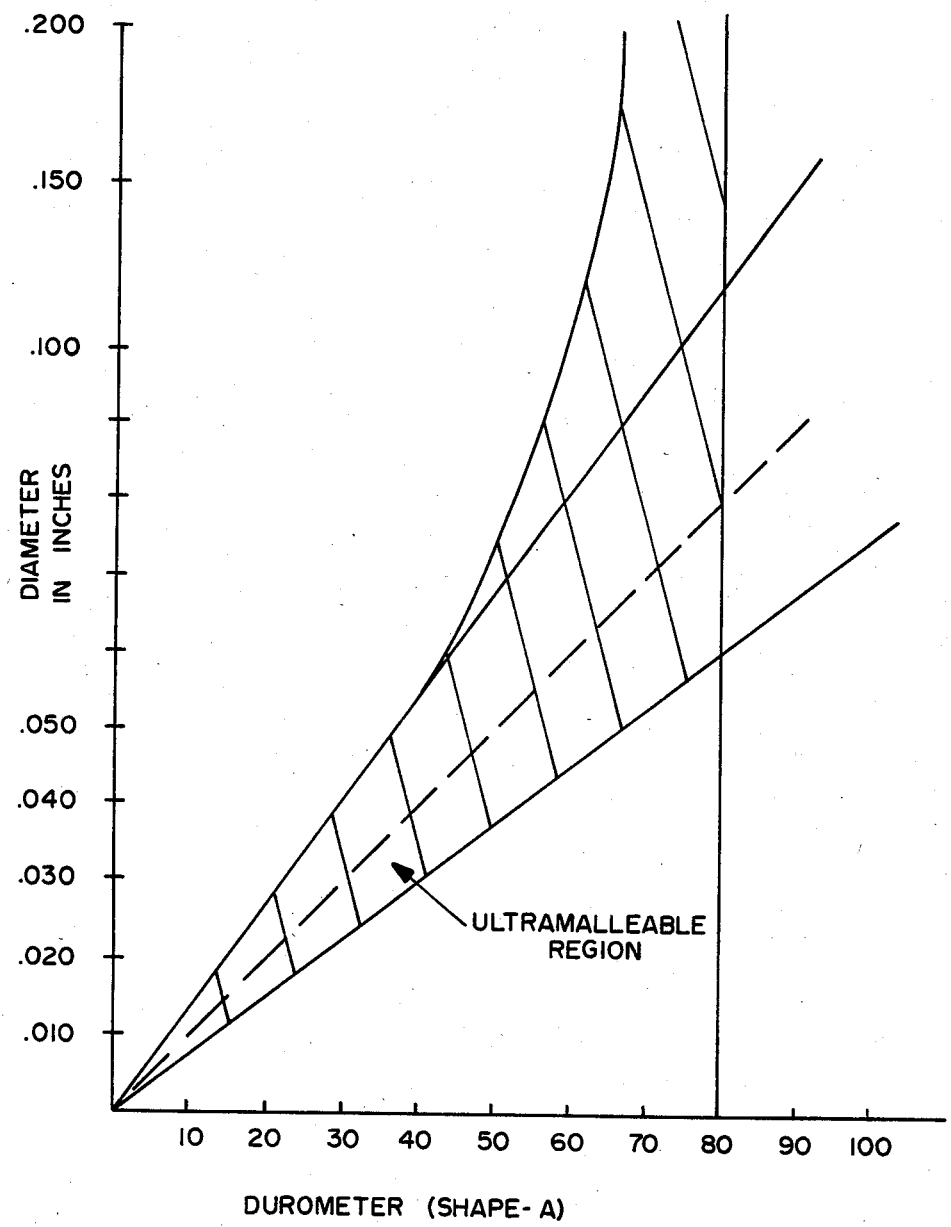
FIG. 12 is a graph of tubing diameter vs. durometer for ultramalleability.

FIGS. 10 and 11 illustrate the 5 French size malleable microsurgical suction device which provides for inherent memory of a predetermined geometrical shape. The MicroVac 100 includes the vacuum connector 102, as is standardly known and available, a round tubing member 104 including inter-round members 106 and 108 secured therein. The multiple perforations at the end include four in number 110a to 110d on opposing sides where four is by way of example and for purposes of illustration only and not to be construed as limiting of the present invention. The tip in this particular example is cut downward at a 30 to 60 degree angle 112 and 114 thereby providing transverse extending inner tips 116 and 118 which is directly behind the inner tip 116. Soft wire 120 runs substantially the length of the inner tube 108. The inner tubes 108 and 106 are opposing each other and are fixed to the inner walls of the larger tube 104. The relationship of the diameter in inches of the tubes with respect to the durometer shape is best illustrated by the graph of FIG. 12 and as later recited in detail. The outer diameter has a proportional wall thickness of 12 percent.

FIG. 11 illustrates a view taken along line 11—11 of FIG. 10 where all numerals correspond to those elements previously described.

FIG. 12 illustrates a graph of the diameter in inches versus the durometer where the lined region is the acceptable ultramalleable region while the upper region is where the tubing collapses and the lower region is where the device is not ultramalleable. This particular relationship is important providing for proper operation of the invention.

Various modifications of the present invention can be made without departing from the apparent scope of the present invention. For instance, the geometrical relationship between the inner area of the tube with respect to the outer diameter of the tube is independent upon the diameter of the outer tube. The particular malleable insert alloy is dependent upon the diameter of the lumen, as well as the diameter of the malleable microsurgical suction device.

Having best described the invention, what is claimed is:

1. A microsurgical suction instrument comprising: a ribbed and tapered mounting member including a chamber running the longitudinal length thereof; a silicone rubber tube connected to the larger diameter end of the mounting member, said tube including three lumens running therethrough, two of said lumens being longitudinally opposed and geometrically symmetrical, a tapered tip, and a plurality of apertures adjacent the tip which extend from one of said three lumens to an outer surface of the tube, said silicone rubber tube having a hardness in a durometer range of about 27-75 and a diameter in the range of about 0.02-0.10 inches, the hardness and diameter being chosen so that the tube is ultramalleable; a connector element for securing the tube into the chamber of the mounting member, said connecting element including a smaller end for encompassing said tube and a larger end for encompassing said larger diameter end of said mounting member; and a malleable wire positioned in and in frictional engagement with one of said two symmetrical lumens, said wire having a length less than the longitudinal length of the tube so as to terminate short of the distal end of the tube; whereby the hardness of the tube as well as the malleability of the wire enable the instrument to be deformable and to retain a predetermined geometrical configuration.

* * * * *